United States Patent
Dolan

(10) Patent No.: US 10,716,738 B2
(45) Date of Patent: Jul. 21, 2020

(54) SOAP INFUSED DISPOSABLE WASHCLOTH DEVICE AND METHOD

(71) Applicant: Roxann Dolan, Bradenton, FL (US)

(72) Inventor: Roxann Dolan, Bradenton, FL (US)

(*) Notice: Subject to any disclaimer, the term of this patent is extended or adjusted under 35 U.S.C. 154(b) by 154 days.

(21) Appl. No.: 15/811,519

(22) Filed: Nov. 13, 2017

(65) Prior Publication Data
US 2018/0133114 A1 May 17, 2018

Related U.S. Application Data

(60) Provisional application No. 62/421,046, filed on Nov. 11, 2016.

(51) Int. Cl.
| | | |
|---|---|---|
| *A47K 7/03* | (2006.01) | |
| *A61K 8/02* | (2006.01) | |
| *A61Q 19/10* | (2006.01) | |
| *C11D 17/04* | (2006.01) | |
| *C11D 9/20* | (2006.01) | |
| *C11D 17/00* | (2006.01) | |

(52) U.S. Cl.
CPC ............. *A61K 8/0208* (2013.01); *A47K 7/03* (2013.01); *A61Q 19/10* (2013.01); *C11D 9/20* (2013.01); *C11D 17/0039* (2013.01); *C11D 17/049* (2013.01); *A61K 8/02* (2013.01); *A61K 2800/28* (2013.01); *C11D 17/041* (2013.01)

(58) Field of Classification Search
CPC ........................................................ A47K 7/03
See application file for complete search history.

(56) References Cited

U.S. PATENT DOCUMENTS

| | | | |
|---|---|---|---|
| 4,935,158 A * | 6/1990 | Aszman | A47L 13/17 15/104.93 |
| 4,948,585 A | 7/1990 | Schlein | |
| 6,806,213 B2 | 10/2004 | Brooks | |
| 7,132,377 B2 | 11/2006 | Borgonjon et al. | |
| 7,381,692 B2 * | 6/2008 | Grissett | A61K 8/0208 510/141 |
| 7,482,021 B1 * | 1/2009 | Tison | A01N 25/34 424/401 |
| 7,589,053 B2 | 9/2009 | Larsen et al. | |
| 9,333,151 B2 * | 5/2016 | Smith, III | A61Q 5/02 |
| 2003/0014824 A1 * | 1/2003 | Farmer | A47K 7/02 15/118 |
| 2004/0040107 A1 * | 3/2004 | Bolkan | A47L 13/16 15/118 |
| 2005/0000046 A1 | 1/2005 | Popovksy et al. | |

(Continued)

*Primary Examiner* — Michael D Jennings
(74) *Attorney, Agent, or Firm* — Acumen Intellectual Property; Michael C. Balaguy

(57) ABSTRACT

A soap infused washcloth device includes a body, the body including a first side, a second side, and an edge. The first side constructed from a first material and the second side of second material. The first material includes a microfiber fabric and the second material includes an abrasive scrubbing material. The body is absorbent such that the body includes soap. The soap includes dry-soap activatable with water such that device remains dry prior to use. Preferably, soap is contained within capsule(s) contained between the first side and the second side of device. The device is removably connected to other soap infused washcloth devices in a linear fashion on a roll. A method of using a soap infused washcloth device is also described.

16 Claims, 5 Drawing Sheets

(56) References Cited

U.S. PATENT DOCUMENTS

| | | | |
|---|---|---|---|
| 2005/0072374 A1* | 4/2005 | Claire | A01K 13/001 119/652 |
| 2005/0113270 A1* | 5/2005 | Stockman | A61K 8/02 510/141 |
| 2006/0016352 A1* | 1/2006 | Copland | A45D 37/00 101/114 |
| 2006/0288954 A1* | 12/2006 | Graunstadt | A01K 13/001 119/652 |
| 2007/0256261 A1* | 11/2007 | Benitez, Jr. | A47K 7/02 15/118 |
| 2015/0238054 A1* | 8/2015 | Green | A47K 7/03 15/104.93 |
| 2016/0095476 A1* | 4/2016 | Morgan | A47K 7/03 15/104.93 |

* cited by examiner

SOAP INFUSED DISPOSABLE WASHCLOTH DEVICE AND METHOD

CROSS-REFERENCE TO RELATED APPLICATION(S)

The present application is related to and claims priority to U.S. Provisional Patent Application No. 62/421,046 filed Nov. 11, 2016, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

Technical Field

The present invention relates generally to the field of woven, knitted, or nonwoven textiles or cloths of existing art and more specifically relates to coated or impregnated fabrics.

Related Art

A wash cloth, washcloth, wash-rag, or face-cloth is a small square or rectangle of absorbent fabric. The wash cloth is generally is used by wetting and applying a soap to the fabric; then using the fabric to apply the soap to skin by scrubbing. This increases abrasion, and can remove dead skin cells from the skin more effectively than just a manual application and rubbing of soap.

A disposable towel is a towel intended for a single user, but it may not be not be necessarily intended for a single use. Disposable towels can be reused in some instances, but generally cannot be washed for reuse. Therefore, it is often made of non-woven fibers such as paper materials or other degradable products. As such, disposable and popular for the hospital, hotel, geriatric, gymnasium, and salon/beauty industries because it increases cleanliness and hygiene. A limitation with disposable towels is that they are generally a paper product that cannot absorb and hold soap and are often non-abrasive. One such limitation with wash cloths is that they provide only a few uses during showering and/or bathing before they must be rewashed to avoid bacteria growth and unhygienic conditions. Further, wash cloths often times provide for an overuse of soap. Therefore, a suitable solution is desired.

U.S. Pat. No. 4,948,585 to Allen P. Schlein relates to a washcloth containing a cleansing agent. The described washcloth containing a cleansing agent includes a disposable washcloth, in one embodiment, formed by impregnating a sheet of non-woven paper with a cured formulation of water activated polyurethane gel, a sudsing detergent, and an aqueous solution of a medicated cleansing agent. In another embodiment the washcloth is made by bonding a sheet of non-woven paper to a sheet of non-woven fabric composed of randomly oriented spray bonded synthetic fibers with the above-mentioned cured formulation. In both cases, the polyurethane dissolves at a slow rate when wetted and controllably releases the detergent and the cleansing agent with modest sudsing.

SUMMARY OF THE INVENTION

In view of the foregoing disadvantages inherent in the known coated or impregnated fabrics art, the present disclosure provides a novel soap infused washcloth device and method. The general purpose of the present disclosure, which will be described subsequently in greater detail, is to provide a soap infused washcloth device and method.

A soap infused washcloth device is disclosed herein. The soap infused washcloth device includes a body, with the body including a first side, a second side, and an edge with the first side affixed to the second side. The first side includes a first material and the second side includes a second material. Preferably, the first material includes a microfiber fabric and the second material includes an abrasive scrubbing material.

The body is absorbent such that the body is impregnatable with soap and the soap infused washcloth device is structured and arranged to wash a body of a user during bathing. The soap includes a dry-soap that is activatable when in contact with water such that the soap infused washcloth device remains dry prior to use. Preferably, the soap is contained within one or more water-soluble capsules which are contained within the first side and the second side of the soap infused washcloth device.

In the preferred embodiment, the soap infused washcloth device is removably connected to other soap infused washcloth devices in a linear fashion such that the user may remove one or more soap infused washcloth devices from a roll. Also the roll is preferably contained within a box.

According to another embodiment, a method of using a soap infused washcloth device is also disclosed herein. The method of use includes a first step, providing a soap infused washcloth device including a body (the body including a first side and a second side, with the body impregnatable with a soap); a second step, wetting the soap infused washcloth device with water; a third step, scrubbing a body of a person with the soap infused washcloth device; a fourth step, rinsing the body of the person; and a fifth step; disposing of the soap infused washcloth device. Note that not all steps are required in all instances, nor are the steps required to be performed in the order above.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a soap infused washcloth device and method, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to coated or impregnated fabrics and more particularly to a soap infused washcloth device and method as used to improve the hygiene and sanitation of washcloths used during bathing.

Generally, a soap infused washcloth device provides users with a disposable washcloth with soap for use during bathing. It may feature a dissolvable liquid capsule or capsules within an abrasive (e.g., loofah) material on one side, allowing soap to penetrate the cloth. It includes smooth microfiber on one side, allowing users to wash themselves in comfort. This eliminates the need to reuse a washcloth which can be unsanitary, especially when multiple washcloths may be left in a shower or bath.

The present invention reduces the amount of soap purchased and wasted while in the bath or shower. The device may be comprised of two sides: one side constructed using a smooth microfiber fabric and the other side constructed of a lace-like device for scrubbing. The device is connected in such a manner that allows multiple variations of the device to be placed in a single container; users can simply tear off a new version of the device each time bathing is required. Users can wash themselves with both sides of the device, as needed, and then simply dispose of the device afterward. Soap infused washcloth device may be available in a universal size and stored within a box or other suitable storage container.

Referring now more specifically to the drawings by numerals of reference, there is shown in FIGS. 1-4, various views of a soap infused washcloth device 100.

Figure 1:
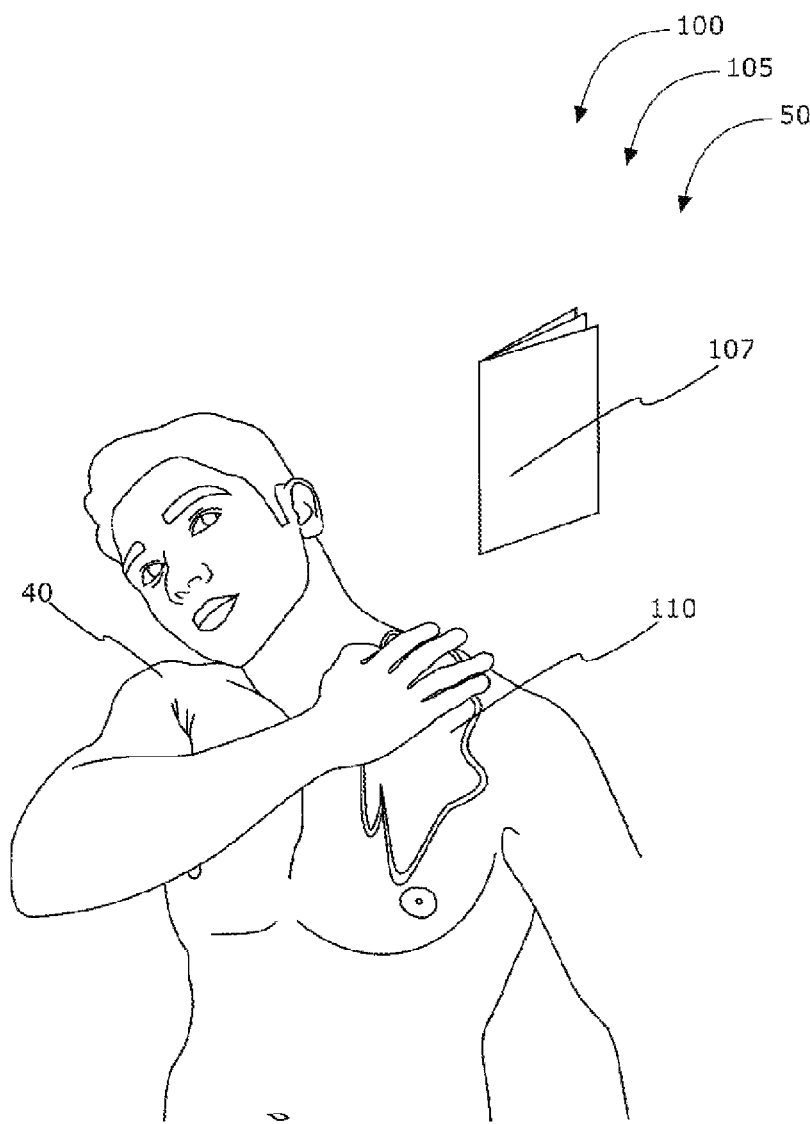
FIG. 1 is a perspective view of the soap infused washcloth device during an 'in-use' condition, according to an embodiment of the disclosure.
Figure 2:
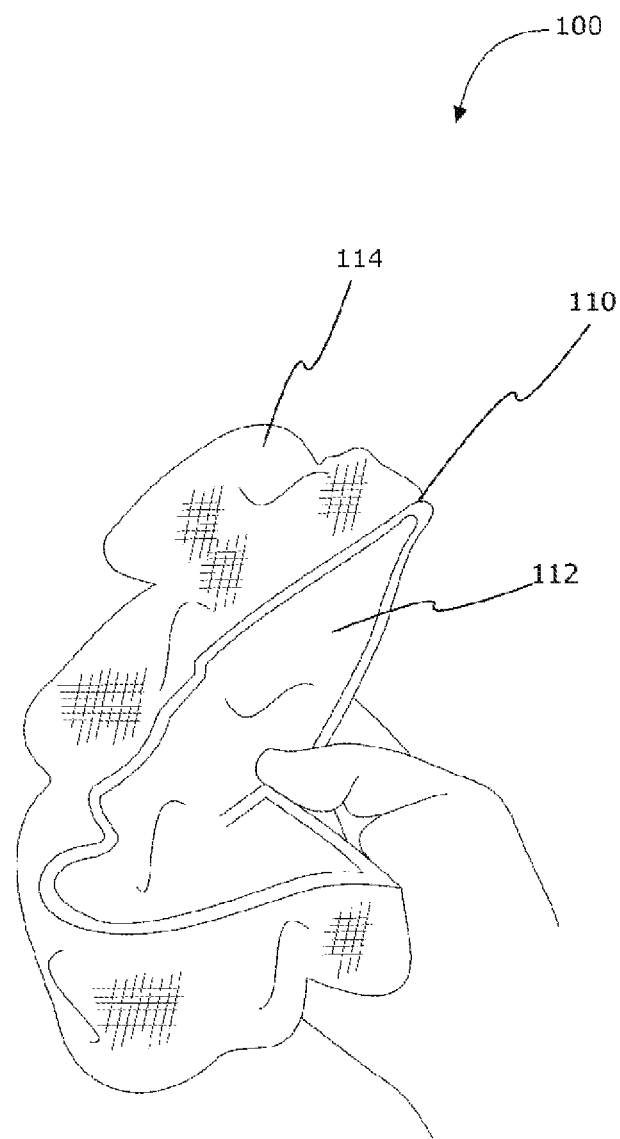
FIG. 2 is a perspective view of the soap infused washcloth device of FIG. 1, according to an embodiment of the present disclosure.
Figure 3:
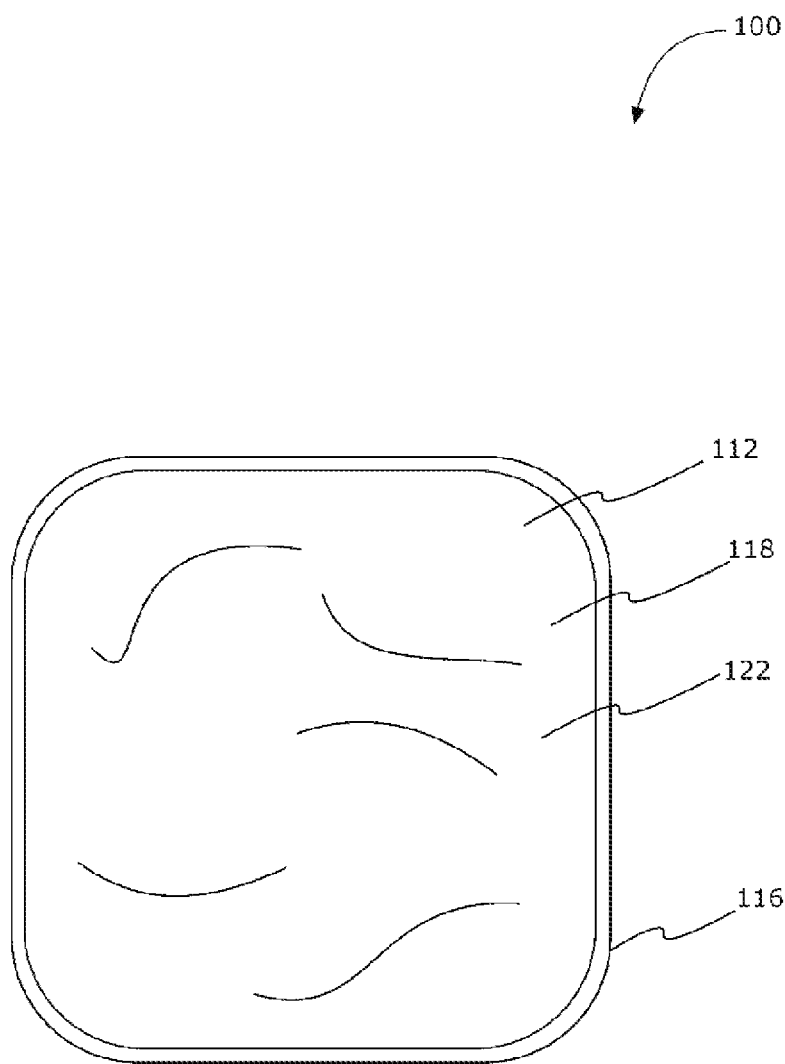
FIG. 3 is a front side view of the soap infused washcloth device of FIG. 2, according to an embodiment of the present disclosure.
Figure 4:
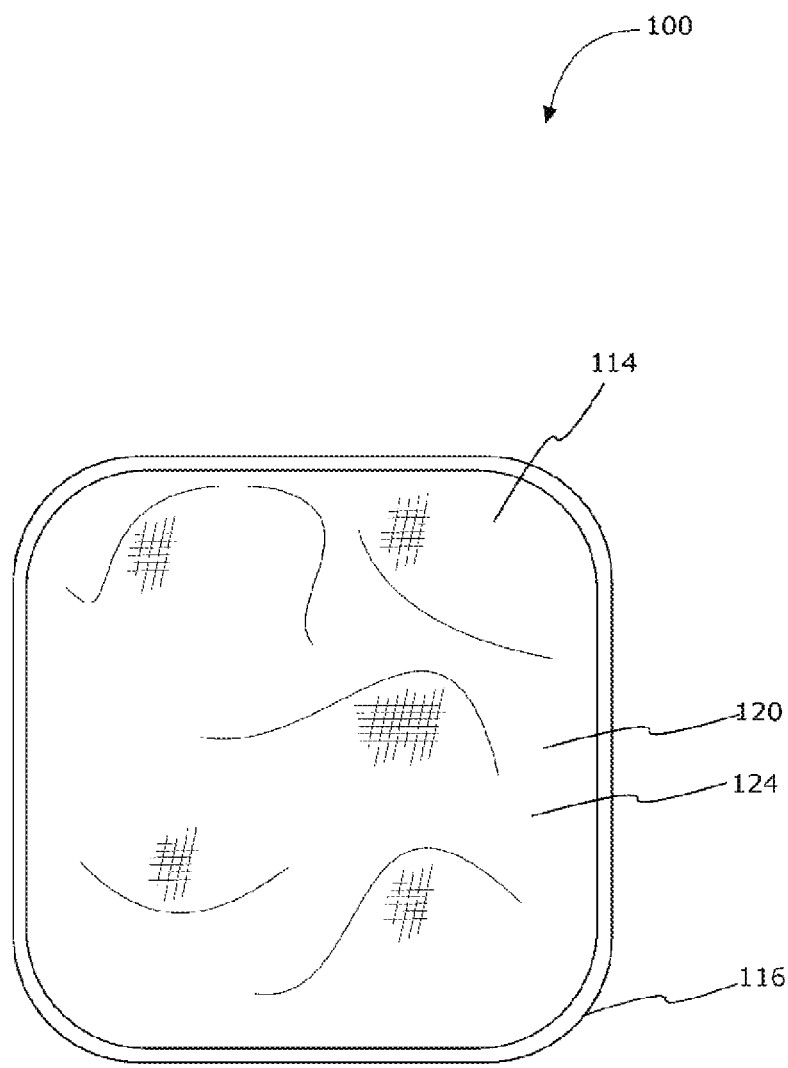
FIG. 4 is a back side view of the soap infused washcloth device of FIG. 2, according to an embodiment of the present disclosure.

FIG. 1 shows a soap infused washcloth device 100 during an 'in-use' condition 50, according to an embodiment of the present disclosure. Here, soap infused washcloth device 100 may be beneficial for use by user 40 to aid in bathing by providing a disposable washcloth to improve sanitation. As illustrated, soap infused washcloth device 100 may include a body 110.

According to one embodiment, soap infused washcloth device 100 may be arranged as a kit 105. In particular, soap infused washcloth device 100 may further include a set of instructions 107. The instructions 107 may detail functional relationships in relation to the structure of soap infused washcloth device 100 such that soap infused washcloth device 100 can be used, maintained, or the like, in a preferred manner.

FIGS. 1-4 show soap infused washcloth device 100 of FIG. 1, according to an embodiment of the present disclosure. As above, the soap infused washcloth device 100 may include body 110, where body 110 may include first side 112, second side 114, and edge 116; with first side 112 affixed to second side 114. First side 112 may include a first material 118, and second side 114 may include a second material 120. Embodiments may include second material 120 that differs from first material 118. Body 110 may be absorbent such that body 110 is impregnatable with soap such that soap infused washcloth device 100 may be structured and arranged to wash a body of user 40 during bathing and/or showering.

First material 118 may include a microfiber material, and second material 120 may include an abrasive and/or scrubbing material (e.g., loofah, etc.), in embodiments. Also, soap infused washcloth device 100 may be constructed from anti-fungal materials in some embodiments. Embodiments of soap infused washcloth device 100 may include instances where device 100 may be disposable. As such, first side 112 and/or second side 114 may be constructed from a biodegradable material in some embodiments. Also, first side 112 and second side 114 may differ in color to provide user 40 with an indicator of side.

The soap of the soap infused washcloth device 100 may include a dry-soap that is activatable upon contact with water. Embodiments may include soap contained within one or more water-soluble capsules contained between first side 112 and second side 114. Also, soap may include a fragrance.

Soap infused washcloth device 100 may be constructed in a wide variety of shapes and/or sizes. As such, soap infused washcloth device 100 may be manufactured in shapes such as rectangles, square, or triangular. Other shapes and sizes may be manufactured dependent upon user preferences. Also, soap infused washcloth device 100 may be connected to other soap infused washcloth devices 100 (e.g., "tear-off", etc.) such that user 40 may remove one or more devices 100 from a roll. The roll may be contained within a box or other suitable vessel. The present invention may be used as an abrasive means.

Figure 5:
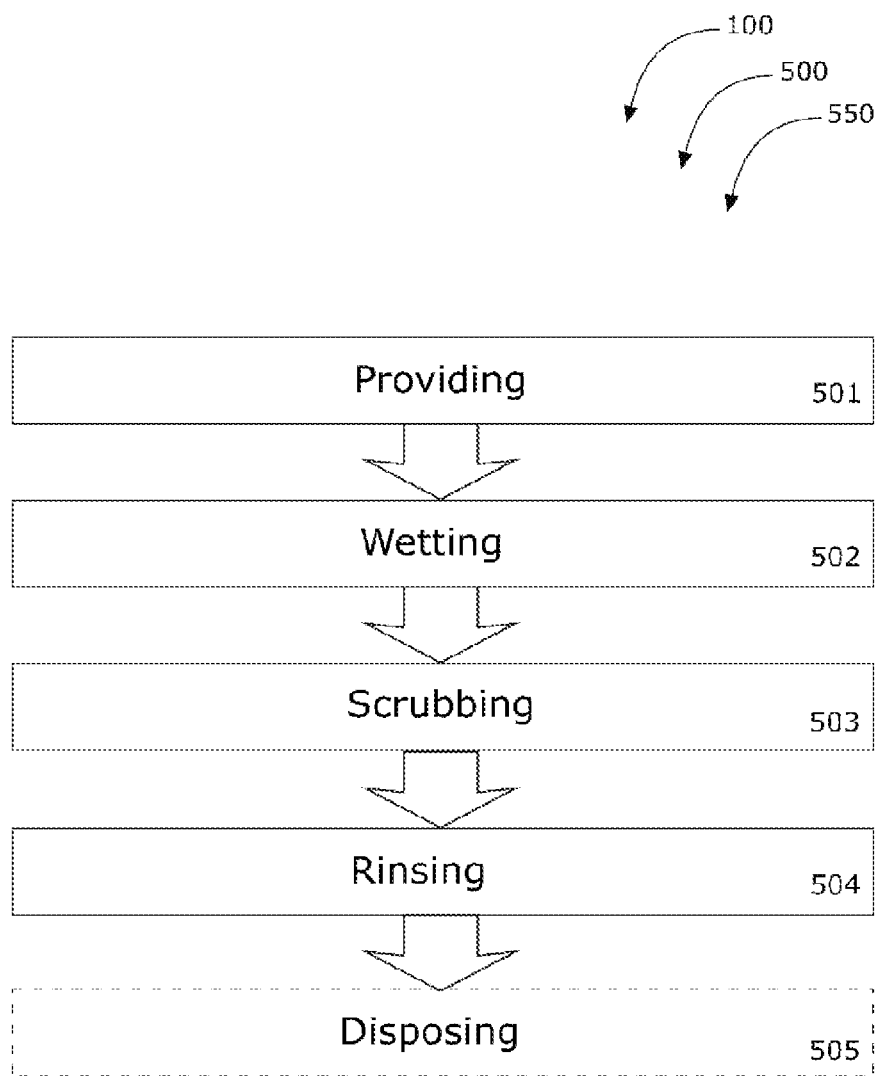
FIG. 5 is a flow diagram illustrating a method of using a soap infused washcloth device, according to an embodiment of the present disclosure.

FIG. 5 is a flow diagram illustrating a method of using a soap infused washcloth device 500, according to an embodiment of the present disclosure. In particular, the method of using a soap infused washcloth device 500 may include one or more components or features of the soap infused washcloth device 100 as described above. As illustrated, the method of using a soap infused washcloth device 500 may include the steps of: step one 501, providing a soap infused washcloth device 100 including body 110, with body 110 including first side 112 and second side 114, with body impregnatable 110 with a soap; step two 502, wetting soap infused washcloth device 100 with water; step three 503, scrubbing a body of a person (user 40) with soap infused washcloth device 100; step four 504, rinsing body of person; and step five 505, disposing of soap infused washcloth device 100.

It should be noted that step five 505 is an optional step and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference.

The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for methods of using a soap infused washcloth device (NOTE: e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A soap infused washcloth system, the system comprising:
    at least two soap infused washcloth devices, each of the at least two soap infused washcloth devices comprising:
        a body, said body comprising a first side, a second side, and an edge defining a rectangle when said body is laid flat;
        wherein said first side includes a first material;
        wherein said second side includes a second material, said second material differing from said first material;
        wherein said first side is affixed to said second side;
        wherein said body is absorbent such that said body is impregnatable with a soap;
        wherein said each of the at least two soap infused washcloth devices are structured and arranged to wash a body of a user during bathing;
        wherein said at least two soap infused washcloth devices are connected in a linear fashion to each other such that said user may remove one or more of the at least two soap infused washcloth devices from a roll.

2. The system of claim 1, wherein said first material includes a microfiber material.

3. The system of claim 1, wherein said second material includes an abrasive scrubbing material.

4. The system of claim 1, wherein said roll is contained within a box.

5. The system of claim 1, wherein said at least two soap infused washcloth devices are disposable.

6. The system of claim 1, wherein said at least two soap infused washcloth devices are constructed from anti-fungal materials.

7. The system of claim 1, wherein said soap includes a dry-soap that is activatable when in contact with water.

8. The system of claim 1, wherein said soap is contained within one or more water-soluble capsules contained between said first side and said second side.

9. The system of claim 1, wherein said first side is constructed from a biodegradable material.

10. The system of claim 1, wherein said second side is constructed from a biodegradable material.

11. The system of claim 1, wherein each of said first side and said second side differ in color to provide said user with an indicator.

12. The system of claim 1, wherein said soap includes a fragrance.

13. The system of claim 1, wherein said soap infused washcloth system is rectangular in shape.

14. The system of claim 1, wherein said soap infused washcloth system is square in shape.

15. A soap infused washcloth system, the system comprising:
    at least two soap infused washcloth devices, each of the at least two soap infused washcloth devices comprising:
        a body, said body comprising a first side, a second side, and an edge defining a rectangle when said body is laid flat;
        wherein said first side includes a first material, said first material including a microfiber material;
        wherein said second side includes a second material, said second material differing from said first material and including an abrasive scrubbing material;
        wherein said first side is affixed to said second side;
        wherein said body is absorbent such that said body is impregnatable with soap;
        wherein said each of the at least two soap infused washcloth devices are structured and arranged to wash a body of a user during bathing;
        wherein said at least two soap infused washcloth devices are connected in a linear fashion such that said user may remove one or more of the at least two soap infused washcloth devices from a roll;
        wherein said roll is contained within a box;
        wherein said soap includes a dry-soap that is activatable when in contact with water; and
        wherein said soap is contained within one or more water-soluble capsules contained between said first side and said second side.

16. The system of claim 15, further comprising set of instructions; and
    wherein the system is arranged as a kit.

* * * * *